US00PP31665P2

(12) United States Plant Patent
Horvath

(10) Patent No.: US PP31,665 P2
(45) Date of Patent: Apr. 14, 2020

(54) ***VERONICA* PLANT NAMED 'KISS THE SKY'**

(50) Latin Name: ***Veronica* hybrid**
Varietal Denomination: Kiss the Sky

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 16/501,495

(22) Filed: Apr. 19, 2019

(51) Int. Cl.
*A01H 5/02* (2018.01)
*A01H 6/68* (2018.01)

(52) U.S. Cl.
USPC ..... Plt./251

(58) Field of Classification Search
USPC ..... Plt./226, 251
See application file for complete search history.

*Primary Examiner* — Susan McCormick Ewoldt
*Assistant Examiner* — Karen M Redden

(57) ABSTRACT

A new, distinct *Veronica* plant as described and illustrated, characterized by the combination of longer stems, longer blue flower spikes, and gray-green.

1 Drawing Sheet

Latin name: *Veronica* hybrid.
Cultivar name: 'Kiss the Sky'.

BACKGROUND OF THE INVENTION

The present invention relates to a new and distinct hybrid of *Veronica* plant named 'Kiss the Sky' characterized by the combination of longer stems, longer blue flower spikes, and gray-green foliage compared to the seed parent. The new *Veronica* was raised as a seedling from open pollinated seed sown from the seed parent *Veronica* x 'Spike' U.S. Plant Pat. No. 27,814, patented, in Hebron, Ill. in 2015. The male, pollen parent is unknown and the new plant was selected as a chance seedling. The selection of the new plant was due to the combination of longer stems, longer blue flower spikes, and gray-green foliage compared to the seed parent. Initial asexual reproduction has taken place at a nursery in Hebron, Ill. since 2016 by means of division, and vegetative stem cuttings. Continued asexual propagation by division and vegetative stem cuttings since that time has shown that the unique features of the new *Veronica* plant are stable and reproduced true to type in successive generations. No plants of the new *Veronica* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

The new *Veronica* plant named 'Kiss the Sky' characterized by combination of longer stems, longer blue flower spikes, and gray-green foliage compared to the seed parent have been observed to be unique and stable. For purpose of comparison the new plant will be referred to as 'Kiss the Sky'.

Plants of 'Kiss the Sky' can be compared to the seed parent plant of *Veronica* x 'Spike', U.S. Plant Pat. No. 27,814. 1. Plants of 'Kiss the Sky' are taller growing to 75-90 cm while *Veronica* 'Spike' grows to 40 cm. 2. 'Kiss the Sky' inflorescence grows to 29 cm in length while

*Veronica* 'Spike' has an inflorescence growing to 23 cm in length.

Plants of 'Kiss the Sky' can also be compared to another *Veronica incana* 'Pure Silver', not patented. 1. The 'Kiss the Sky' plant has longer inflorescence growing to 29 cm in length, while *Veronica incana* 'Pure Silver' inflorescence grow to 10 cm in length. 2. The 'Kiss the Sky' plant has a flower color of RHS N88 B while *Veronica incana* 'Pure Silver' has a flower color of N89 A.

DESCRIPTION OF PHOTOGRAPHS

Figure 1:
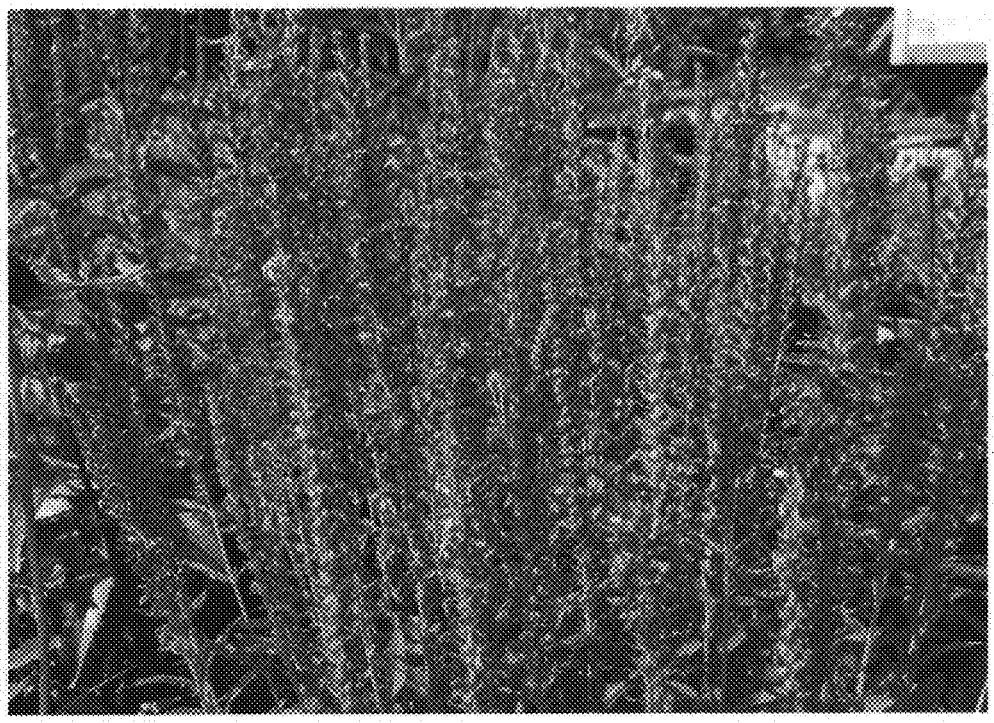
Figure 2:
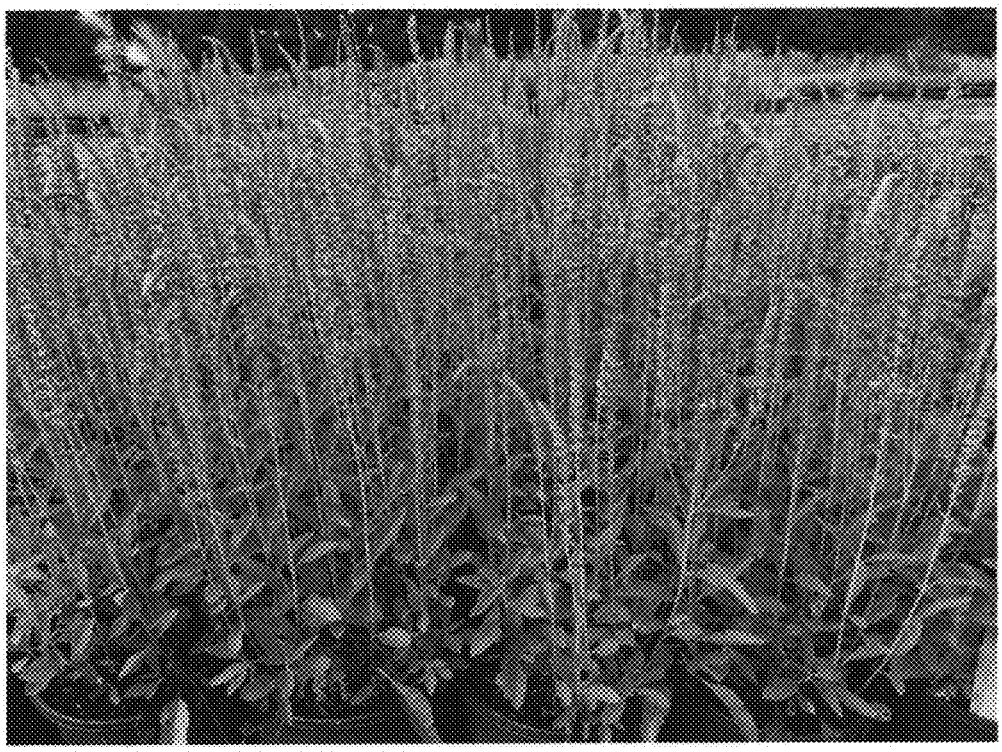

Plants pictured in the drawing were grown for one year.
FIG. 1. Close up of the flower spike.
FIG. 2. A group of plants.

DETAILED BOTANICAL DESCRIPTION

In the following description, color references are made to The Royal Horticultural Society Colour Chart (2001). Plants used for the description were grown for one year at a nursery in Hebron, Ill. Measurements and numerical values represent averages of typical plants.

Plant:
- *Botanical classification.*—*Veronica* hybrid.
- *Parentage.*—Female (seed parent) *Veronica* x 'Spike', Male parent, unknown.
- *Form.*—Upright.
- *Plant height.*—75-90 cm from soil to top of flowers; width: 60 cm wide.
- *Growth.*—Herbaceous perennial, upright, good vigor.
- *Roots.*—Fibrous.

Stem:
- *Form.*—Cylindrical, branching from the base, no pinching required.
- *Color.*—Close to N199 A at the base, 147 C at the top half.
- *Surface texture.*—Glabrous.
- *Length.*—75-90 cm.
- *Diameter.*—4 mm wide.
- *Flower stem internode length.*—3-4 cm.
- *Internode quantity.*—Typically 5.

Foliage:

*Arrangement.*—Opposite.

*Number of leaves per basal stem.*—12, 6 pairs.

*Size of leaf.*—Length: 8-10 cm on average, decreasing in both length and width distally. Width: 3.5 cm.

*Shape of leaf.*—Lanceolate.

*Shape of tip.*—Acute.

*Shape of base.*—Rounded to slightly attenuate.

*Texture.*—Glabrous.

*Margin type.*—Serrate.

*Color.*—Young and Mature leaves: Upper surface: 137 A. Lower surface: close to 148 B.

*Petioles.*—Glabrous. Length: 35 mm on average for lower leaves; 10 mm on average for other leaves. Diameter: 2 mm. Color: Adaxial 147 C, Abaxial between 147 b and C. Surface: Adaxial glabrous, Abaxial glabrous.

*Veins.*—Pattern: Pinnate with a pronounced mid-vein on the lower surface and depressed on the upper leaf surface. Color: Upper surface: 137 A. Lower surface: 147 C.

Flower:

*Natural flowering season.*—Continuous from mid to late July into August.

Inflorescence type and habit: Branched, terminal spike, no fragrance, flowers last about 5 days on plant. Rate of flower opening: About 25% of flowers open at once, all flowers open in about 4 weeks.

Type of flower: Tubular with four petal lobes.

Number of flowers: About 75 per spike; about 50 per lateral branch.

Inflorescence size:

*Diameter of an inflorescence.*—18 mm. Height. — 29 cm.

*Length of terminal spike.*—29 cm.

*Individual flower size.*—7 mm long, 7 mm wide.

Peduncle:

*Length.*—11 cm. Diameter. — 2 mm.

*Color.*—148 B with some aging to N199 B at the base.

*Orientation.*—Upright with 4-5 secondary peduncles at 30-45°.

*Strength.*—Strong.

*Surface.*—Glabrous

Pedicel:

*Length.*—1-2 mm long, less than 1 mm wide, close to 0.5 mm, Color. — 146 D.

Petals:

*Petal arrangement.*—One larger above three slightly smaller.

*Large petal size.*—7 mm long; 3 mm wide. Small petal size. — 7 mm long; 2 mm wide.

*Margin.*—Entire.

*Tip shape.*—Emarginate upper lip; rounded lower lip.

*Length.*—Average upper lip: 3 mm; average lower lip: 3 mm.

*Width.*—Average upper lip: 3 mm; average lower lip: 2 mm.

*Petal quantity.*—4.

*Petal texture.*—Glabrous.

*Corolla.*—Length: 3 mm long, width: 3 mm wide, Color: N88 B.

*Petals.*—When opening: Upper surface: N88 B. Lower surface: N88 B. Fully opened: N88 B. Lower surface: N88 B.

Bud:

*Shape.*—Convolute, narrowly oblong, obtuse apex.

*Length.*—6 mm. and Diameter. — 2 mm. Color — N88 B.

Calyx:

*Arrangement.*—4 free sepals.

*Height.*—4 mm.

*Diameter.*—1-2 mm.

*Shape.*—Free.

*Sepals.*—Shape: ovate, acute apex, base fused forming corolla. Size: Average 4 mm long; 1 mm wide. Margin: Entire. Texture: glabrous. Color: Outer surface: N88 B. Inner surface: N88 B.

*Bracts.*—None observed.

Reproductive organs:

Stamens:

*Number.*—2.

*Filament length.*—7 mm.

*Anthers.*—Shape: Basifixed, elliptic. Length: 1-2 mm. Width 1 mm. Color: N85 C.

*Pollen.*—Color: white 155 C Amount: low.

Pistil:

*Number.*—One.

*Length.*—7 mm, less than 1 mm wide.

*Style.*—Length: 8 mm. Color: N88 B at the top half fading to white at the base.

*Stigma.*—Shape: cylindrical. Color: 77 A. Ovary color: N77 C and 147 C at the base.

Seeds: Brown and round 2 mm long and 1 mm wide, color 200 B.

Disease/pest resistance: No unusual susceptibility to diseases or pests has been noted.

Temperature tolerance: Tolerate to heat at least up to 30° C. and cool at least down to USDA Zone 4-8.

I claim:

1. A new, distinct *Veronica* plant as described and illustrated, characterized by the combination of longer stems, longer blue flower spikes, and gray-green foliage compared to the seed parent.

* * * * *